United States Patent [19]

Buder et al.

[11] 4,129,585
[45] Dec. 12, 1978

[54] PROCESS FOR THE PRODUCTION OF SULFUR CONTAINING ORGANOSILICON COMPOUNDS

[75] Inventors: Wolfgang Buder, Rodenbach, Germany; Hans-Dieter Pletka, Mobile, Ala.; Rudolf Michel, Freigericht, Germany; Rudolf Schwarz, Wasserlos, Germany; Gerhard Düsing, Eppstein, Germany

[73] Assignee: Deutsche Gold- und Silber-Scheideanstalt vormals Roessler, Frankfurt, Germany

[21] Appl. No.: 884,212

[22] Filed: Mar. 7, 1978

[30] Foreign Application Priority Data

Mar. 24, 1977 [DE] Fed. Rep. of Germany ....... 2712866

[51] Int. Cl.$^2$ .......................... C07F 7/18; C07F 7/10; C07F 7/08
[52] U.S. Cl. ..................... 260/448.8 R; 260/448.2 N
[58] Field of Search .................. 260/448.2 E, 448.8 R

[56] References Cited

U.S. PATENT DOCUMENTS

| | | | |
|---|---|---|---|
| 3,946,059 | 3/1976 | Janssen et al. ................ | 260/448.2 E |
| 3,957,844 | 5/1976 | Mui ................ | 260/448.2 E |
| 3,997,581 | 12/1976 | Pletka et al. .................. | 260/448.8 R |
| 4,072,701 | 2/1978 | Pletka et al. .................. | 260/448.8 R |

Primary Examiner—Paul F. Shaver
Attorney, Agent, or Firm—Cushman, Darby & Cushman

[57] ABSTRACT

There is provided a process for the production of sulfur containing organosilicon compounds of the formula (I) Z — Alk — $S_x$ — Alk — Z, where Z is the grouping:

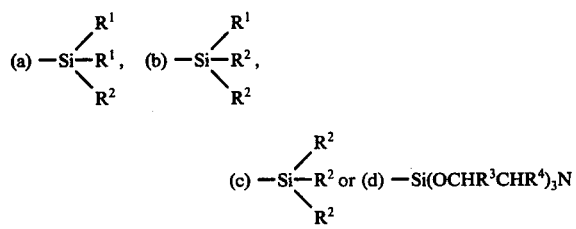

in which $R^1$ is an alkyl group having 1 to 5 carbon atoms, a cycloalkyl group with 5 to 8 carbon atoms, the benzyl group, phenyl or phenyl substituted with at least one methyl, ethyl or chloro group, $R^2$ is alkoxy of 1 to 4 carbon atoms, methoxyethoxy, cycloalkoxy with 5 to 8 carbon atoms, phenoxy or benzyloxy, $R^3$ and $R^4$ are alkyl of 1 to 3 carbon atoms or hydrogen, Alk is divalent saturated hydrocarbon group having 1 to 5 carbon atoms or such a group interrupted by —O—, —S— or —NH— and x is a number from 2.0 to 6.0 comprising reacting an alkali metal alcoholate, preferably in alcoholic solution with a compound of the formula (II) Z — Alk — Hal, where Hal is chlorine, bromine or iodine with a hydrosulfide of the formula (III) MeSH, in which Me is ammonium, an alkali metal atom or an equivalent of an alkaline earth metal or zinc and with sulfur, preferably in the presence of at least one organic solvent, separating from the halide formed, and removing the organic solvent.

12 Claims, No Drawings

PROCESS FOR THE PRODUCTION OF SULFUR CONTAINING ORGANOSILICON COMPOUNDS

BACKGROUND OF THE INVENTION

The present invention is directed to the production of sulfur containing organosilicon compounds by a new process which can be carried out in a simple, safe and problem free manner from readily available starting materials without the formation of toxic by-products and with a practically quantitative progress of the reaction.

There is known a process for the production of bis-(alkoxysilylalkyl)-oligosulfides from the corresponding alkoxysilylalkyl halogenides by reacting with alkali metal oligosulfides, preferably in alcoholic solution (Belgian Pat. No. 787,691 and related Meyer-Simon U.S. Pat. No. 3,842,111 as well as Thurn U.S. Pat. No. 3,873,891). The alkoxysilylalkyl halides in turn are obtained from the halosilylalkylhalides in conventional manner by alcoholysis. The entire disclosures of Meyer-Simon and Thurn are hereby incorporated by reference and relied upon.

There has also been proposed in Pletka application Ser. No. 730,726, filed Sept. 24, 1976 and now U.S. Pat. No. 4,072,701, a process for the production of bis-(alkoxysilylalkyl)-oligosulfides from halosilylalkyl halides by reaction with an alcohol, alkali metal hydrosulfide and sulfur in a so-called one kettle reaction wherein hydrogen sulfide is formed as by-product so that a part, one mole, of the sulfur added is not utilized for incorporation into the molecule of the oligosulfide. The hydrogen sulfide cannot be recovered in practice, but also cannot be released to the atmosphere. The entire disclosure of the Pletka application is hereby incorporated by reference and relied upon.

The problem of the present invention was to eliminate this disadvantage and to find a process giving as close to quantitative yield as possible without forming toxic or environmentally undesirable by-products.

SUMMARY OF THE INVENTION

This problem was solved by producing organosilicon compounds of the formula (I) Z - Alk - $S_x$ - Alk - Z, in which Z is the group:

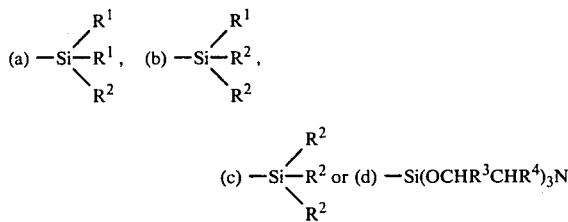

in which $R^1$ is a straight or branched chain alkyl group of 1 to 5 carbon atoms, a cycloalkyl group with 5 to 8 carbon atoms, the benzyl group, phenyl or phenyl substituted with methyl, ethyl or chloro groups, $R^2$ is an alkoxy group having a straight or branched carbon chain with 1 to 4 carbon atoms, the methoxy-ethoxy group, a cycloalkoxy group with 5 to 8 carbon atoms, the phenoxy group or the benzyloxy group, wherein $R^1$ and $R^2$ can be the same or different, $R^3$ and $R^4$ are the same or different and are hydrogen, methyl, ethyl, n-propyl or i-propyl, Alk is a divalent saturated hydrocarbon group, e.g., alkylene, with 1 to 5 carbon atoms which can be in a straight or branched carbon chain which can be interrupted, e.g., once or twice, by —O—, —S— or —NH—, and x is a number from 2.0 to 6.0. The process comprises reacting an alkali metal alcoholate in preferably alcoholic solution with a compound of the formula (II) Z — Alk — Hal, in which z is as defined above and Hal is a chlorine, bromine or iodine atom (i.e., halogen of atomic weight 35 to 127), with a hydrosulfide of the formula (III) MeSH in which Me is an alkali metal atom, e.g., sodium, potassium, rubidium or cesium, ammonium or one equivalent of an alkaline earth metal or of zinc, e.g., magnesium, calcium, barium or strontium or zinc and reacting with sulfur, preferably in the presence of at least one organic solvent, separating from the halide formed and then removing the organic solvent (if used). The amount of sulfur should be sufficient together with the sulfur in MeSH to satisfy the value of x in formula (I).

The starting material (II), i.e., the haloalkoxysilane is produced in known manner such as by hydrosilation of single unsaturated halohydrocarbon as for example by addition of trichlorosilane to allyl chloride in presence of a noble metal catalyst, e.g., palladium or platinum, with subsequent alcoholysis of the trichlorosilylpropyl chloride whereby generalized represented →Si - Hal bonds in the molecular are changed into a →SiOR bond where R is the alkyl group of the alcohol. In place of allyl chloride there can be used, for example, allyl bromide, allyl iodide, vinyl chloride, vinyl bromide, methallyl chloride, 1-chlorobutene-3, 1-chloropentene-4.

If the halosilane contains three OR groups it can likewise according to known process using a transesterification catalyst be reacted with triethanolamine or a triethanolamine substituted on a carbon atom with an alkyl group to form a haloalkylsilatrane.

In general formula (II) Hal indicates a halogen atom, particularly chlorine, bromine or iodine, preferably chlorine. Halosilanes within formula (II) include, for example, chloromethyltrimethoxysilane, 2-chloroethyldiethoxyethylsilane, 2-bromoethyltri-i-propoxysilane, 2-chloroethyltriethoxysilane, 3-chloropropyltrimethoxysilane, 3-chloropropyldiethoxymethylsilane, 3-chloropropylcyclohexoxydimethylsilane, 4-bromobutyldiethoxybenzylsilane, 4-iodobutyltrimethoxysilane, 5-chloropentyldimethoxyphenylsilane, 3-bromo-i-butyltriethoxysilane, 3-chloropropyl-dimethoxy-p-chlorophenylsilane, 2-chloro-i-propyl-diethoxy-p-ethylphenylsilane, 3-chloropropylethoxymethylethylsilane, 5-iodo-n-pentyl-diethoxycyclopentylsilane, 3-bromopropyldimethoxycyclopentoxysilane, 2-chloro-2'-methylethyldiethoxycycloheptoxysilane, 3-bromo-2'-methylpropyldimethoxycyclooctylsilane, 3-chloropropyldiethoxy-2'-methoxy-ethoxy-silane, 2-chloroethyldimethylcyclooctyloxysilane, 3-chloropropyldibutoxymethylsilane, 3-bromopropylphenyloxydimethoxysilane, 3-chloropropyldi-i-butoxy-2'-methylphenylsilane, 3-chloro-3'-methyl-propyl-dimethoxybenzyloxysilane, 3-chloropropyltributoxysilane, 3-chloropropyldiethoxyamylsilane and 3-chloropropyldiethoxy-p-methylphenylsilane.

The alkali metal component of the alcoholate is preferably potassium or sodium, most preferably sodium while the alcohol component is preferably an aliphatic primary alcohol, e.g., an alkanol such as methyl alcohol, ethyl alcohol, propyl alcohol, isopropyl alcohol, butyl alcohol, amyl alcohol, hexanol-1, octanol-1, etc. Suitably there is used freshly prepared alcoholate with excess alcohol whereby this alcohol or a mixture of alcohols serves at the same time as solvent for the reaction. Thereby advantageously the alcohol or a portion thereof arises from the above mentioned alcoholysis process.

In general formula (III) Me particularly signifies the ammonium group, sodium, potassium or one equivalent of the metals magnesium, calcium, strontium, barium or zinc. In carrying out the process of the invention there are preferably used as compounds of formula (III) sodium hydrosulfide, potassium hydrosulfide, calcium hydrosulfide or ammonium hydrosulfide. They are preferably added in the most finely divided form, for example, as powders.

In formulae (I) and (II) Alk indicates methylene as well as preferably ethylene, i-propylene, n-propylene, i-butylene, n-butylene or n-amylene. Alk can also have the following meaning: $-CH_2-S-CH_2-$; $-CH_2-O-CH_2-$; $-CH_2-NH-CH_2-$; $-CH_2-S-CH_2CH_2-$; $-CH_2-O-CH_2CH_2-$; $-CH_2-NH-CH_2CH_2-$; $-CH_2CH_2-S-CH_2CH_2-$; $-CH_2CH_2-O-CH_2CH_2-$; $-CH_2CH_2-NH-CH_2CH_2-$; $-CH_2-S-CH_2-S-CH_2-$; $-CH_2-O-CH_2-O-CH_2-$; $-CH_2-NH-CH_2-NH-CH_2-$; $-CH_2-S-CH_2CH_2-S-CH_2-$; $-CH_2-O-CH_2CH_2-O-CH_2-$; $-CH_2-NH-CH_2CH_2-NH-CH_2-$; $-CH_2CH_2-S-CH_2-S-CH_2CH_2-$; $-CH_2CH_2-O-CH_2-O-CH_2CH_2-$; $-CH_2CH_2-NH-CH_2-NH-CH_2CH_2-$.

To carry out the reaction of the invention the elemental sulfur is advantageously added in finely divided form, for example, as sulfur powder. To accelerate the running of the reaction the hydrosulfide is also preferably added in powder form. The reaction generally begins even at room temperature after the reactants are brought together and it can be continued further by itself as an exothermic reaction. Suitably to shorten the total reaction time the operation is carried out at elevated or increasing temperature which can rise to the boiling point of the solvent or solvent mixture used. Especially advantageous is the use of an inert organic solvent of not too high boiling point, which is capable of dissolving the reactants wholly or in part. Such solvents include, for example, dioxane, dimethyl formamide, tetrahydrofuran and particularly acetone as well as preferably alcohols, especially primary lower aliphatic alcohols or cycloaliphatic alcohols, e.g., methyl alcohol, ethyl alcohol, isopropyl alcohol, and n-butyl alcohol, cyclohexanol and cyclopentanol as well as mixtures of such alcohols.

Furthermore, it is advantageous to carry out the reaction while excluding air and/or water (moisture) to suppress the formation of by-products or to substantially avoid their formation. One can operate for example under a dry inert gas such as nitrogen or under a noble gas, e.g., argon, neon or helium. It can also be suitable to carry the reaction under reduced pressure or slightly elevated pressure.

In the new reaction, in contrast to the earlier mentioned reaction, employing only a hydrogen sulfide and sulfur, there is formed no hydrogen sulfide which must be burned catalytically to avoid polluting the environment if it is not recycled for use or needed in another way. In the reaction there are formed only the alkali metal halide and alcohol which are recovered together with the alcohol solvent. The course of the reaction goes practically quantitatively according to the following equation:

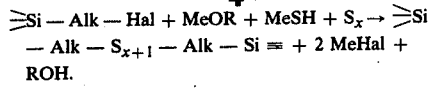

From this equation there can also be seen the molar amounts of the compounds to be added and of sulfur. The exothermic reaction generally begins at moderate temperatures of 20° to 80° C. and suitably toward the end of the reaction is carried out at the reflux temperature. A certain post reaction time is also advantageous. After the end of the reaction, the reaction mixture is cooled, filtered off from the separated salt and then the organic solvent or mixture of solvents advantageously removed by distillation, suitably under reduced pressure. The sulfur containing organosilicon compounds formed as the final product cannot be distilled under conventional conditions without decomposition. In practice they are collected in the sump of the distillation unit and in most cases can be supplied directly to the desired use without purification. For example, they can be added as valuable adhesive aids or reinforcing additives in silicate filler containing rubber mixtures. However, they are valuable intermediate products.

The poly or oligosulfidic silanes of formula (I) for the most part are known (see Belgian Pat. No. 787,691 as well as related Meyer-Simon U.S. Pat. No. 3,842,111 as well as Thurn U.S. Pat. No. 3,873,489). However, the compounds are made by other processes than that of the present invention. Also, it has already been proposed to produce these silanes by direct reaction of mercaptoalkylsilanes with sulfur (German OS No. 2,405,758 and related Pletka U.S. Pat. No. 3,997,581. The entire disclosure of Pletka is hereby incorporated by reference and relied upon.). In Janssen German Offenlegungsschrift No. 2,360,471 there is described a process in which the corresponding polysulfides are obtained by building elemental sulfur into organosilylalkyl disulfides. However, this process has several strong disadvantages compared to the process of the present invention. While in the process of the invention one starts with the easily available haloalkylsilanes and obtained the polysulfides in one reaction step, according to the known process the mercaptoalkylsilanes must be first produced from these haloalkylsilanes and then there is produced by oxidation in a further reaction step the necessary disulfides employed as starting materials. Furthermore, the reaction times of 15 to 50 hours at reaction temperatures around 150° C. are a further disadvantage. In contrast to these known syntheses the process of the invention is surprisingly simple. The expenditure for apparatus and time in carrying out the new process is very small and the running of the reaction is practically quantitative. The new process with easily available starting materials is clearly superior to all previously known processes from an industrial and economical viewpoint.

Preferred silanes according to formula (I) are: the bis-[trialkoxysilyl-alkyl-]-polysulfides such as the bis-trimethoxy-, -triethoxy-, -tri-(2-methoxyethoxy)-, -tripropoxy-, -tri-i-propoxy-, -tributoxy-, etc., up to the -tripentoxysilylmethyl]-polysulfides; furthermore the bis-[2-trimethoxy-, -triethoxy-, -tri-(2-methoxyethoxy)-, -tripropoxy-, -tri-i-propoxy-, -tributoxy-, etc., up to the tripentoxysilyl-ethyl]-polysulfides namely, the di-, tri-, tetra-, penta- and hexasulfide, preferably the bis-[3-trimethoxy-, -triethoxy-, -tri-(2-methoxyethoxy)-, -tripropoxy-, -tri-i-propoxy-, -tributoxy-, etc., up to the -tripentoxysilylpropyl]-polysulfides, again the di-, tri-, tetra-, etc., up to the hexasulfides; furthermore the corresponding bis-[3-trialkoxysilyl-isobutyl]-polysulfides, the corresponding bis-[4-trialkoxysilylbutyl]-polysulfides, etc., up to the bis-[5-trialkoxysilylpentyl]-polysulfides. Of those selected there are preferred the relatively simple organosilanes of formula (I), such as the bis-[3-trimethoxy-, -triethoxy- and -tripropoxysilylpropyl]-polysulfides, preferably the tri-, tetra- and pentasulfide. Examples of silanes of formula (I) produced according to the invention include bis-(3-trimethoxysilylpropyl)-trisulfide, bis-(3-triethoxysilylpropyl)-tetrasulfide, bis-(3-trimethoxysilylpropyl)-tetrasulfide, bis-(2-triethoxysilylethyl)-tetrasulfide, bis-(3-trimethoxysilylpropyl)-disulfide, bis-(3-triethoxysilylpropyl)-trisulfide, bis-(3-tributoxysilylpropyl)-pentasulfide, bis-(3-trimethoxysilylpropyl)-hexasulfide, bis-(3-tricyclooctoxysilylpropyl)-tetrasulfide, bis-(3-triphenoxysilylpropyl)-pentasulfide, bis-[3-tris-(2-ethylhexoxy)-silylpropyl]-tetrasulfide, bis-tri-(3-isobutoxysilylpropyl)-tetrasulfide, bis-(tris-t-butoxysilylmethyl)-trisulfide, bis-(2-methoxydiethoxysilylethyl)-tetrasulfide, bis-(2-tri-i-propoxysilylethyl)-pentasulfide, bis-(3-tricyclohexoxysilylpropyl)-tetrasulfide, bis-(3-tricyclopentoxysilylpropyl)-trisulfide, bis[2-tris-(4'-methylcyclohexoxy)-silylethyl]-tetrasulfide, bis-(dimethoxyphenoxysilylmethyl)-tetrasulfide, bis-(3-dimethoxymethylsilylpropyl)-di-, -tri- and tetrasulfides, bis-(3-dimethoxyethylsilylpropyl)-di-, -tri- and -tetrasulfides, bis-(3-diethoxymethylsilylpropyl)-di-, -tri- and -tetrasulfides, bis-(3-diethoxyethylsilylpropyl)-di-, -tri- and -tetrasulfides, bis-(3-methoxydimethylsilylpropyl)-di-, -tri- and -tetrasulfides, bis-(3-ethoxydimethylsilylpropyl)-di-, -tri- and -tetrasulfides, bis-(3-diethylethoxysilylpropyl)-tetrasulfide, bis-(2-dimethoxymethylsilylethyl)-disulfide, bis-(3-di-i-propoxymethylsilylpropyl)-di-, -tri- and -tetrasulfides, bis-(3-di-i-propoxyethylsilylpropyl)-di, -tri-, and -tetrasulfides, bis-(4-diethoxyethylsilylbutyl)-trisulfides, bis-(5-triethoxysilylpentyl)-pentasulfide, bis-(5-phenyldimethoxysilylpentyl-tetrasulfides, bis-(4-triethoxysilylbutyl)-hexasulfide, bis-[4-ethylbis-(methoxyethoxy)-silyl-butyl]-tetrasulfide, 3-methoxyethoxypropoxysilylpropyl-3'-dimethoxyethoxysilylpropyltetrasulfide, bis-(4-methyl-dimethoxysilylbutyl)-pentasulfide, bis-(2-dimethoxyphenylsilylethyl)-trisulfide, bis-(3-methylbutylethoxysilylpropyl)-tetrasulfide, bis-(2-ethyldiethoxysilyl-i-propyl)-tetrasulfide, bis-(3-silatranopropyl)-di-, -tri-, -tetra-, -penta- and -hexasulfide, bis-(2-silatranoethyl)-di-, -tri- and -tetrasulfide, bis-(2-silatrano-i-propyl)-di-, -tri- and -tetrasulfide as well as, for example, bis-(3-silatrano-i-butyl)-di-, -tri- and -tetrasulfide.

There are also included within the invention the preparation of any of the other compounds within formula (I) disclosed in Meyer-Simon U.S. Pat. No. 3,842,111 and Thurn U.S. Pat. No. 3,873,489, Pletka U.S. Pat. No. 3,997,581 and Pletka U.S. application Ser. No. 730,726 filed Sept. 24, 1976. Other compounds which can be mentioned include bis(3-triscyclooctoxysilylpropyl)-tetrasulfide, bis(3-triphenoxysilylpropyl)-trisulfide, bis(2-diphenoxybenzyloxysilylethyl)-tetrasulfide, bis(3-tribenzyloxysilylpropyl)-pentasulfide, bis(3-dimethoxy-p-ethylphenylsilylpropyl)-tetrasulfide, bis(3-dimethoxy-p-chlorophenylsilylpropyl)-tetrasulfide, bis(3-diethoxy-4',5'-dichlorophenylsilylpropyl)-trisulfide, bis(3-dimethoxy-3',4'-dimethylphenylsilylpropyl)-trisulfide, bis(3-propoxy-diphenylsilylpropyl)-tetrasulfide, bis(2-diethoxy-p-tolylsilylethyl)-tetrasulfide, bis(3-dipropoxybenzylsilylpropyl)-tetrasulfide.

In addition to the meanings set forth above, Alk also can have the following meanings: —CH$_2$—S—CH$_2$CH$_2$—S—CH$_2$—; —CH$_2$—O—CH$_2$CH$_2$—O—CH$_2$—; —CH$_2$—NH—CH$_2$CH$_2$—NH—CH$_2$—; —(CH$_2$)$_2$—S—CH$_2$—S—(CH$_2$)$_2$—; —(CH$_2$)$_2$—O—CH$_2$—O—(CH$_2$)$_2$—; —(CH$_2$)$_2$—NH—CH$_2$—NH—(CH$_2$)$_2$—; —CH$_2$—O—CH$_2$CH(CH$_3$)—O—CH$_2$—; —(CH$_2$)$_2$—NH—(CH$_2$)$_2$—; —(CH$_2$)$_2$—O—(CH$_2$)$_2$—; —CH(CH$_3$)—S—CH(CH$_3$)—; —CH$_2$—O—CH$_2$—; —CH$_2$—S—CH$_2$—; —CH$_2$—NH—CH$_2$—; —CH$_2$—O—CH$_2$—O—CH$_2$—.

Examples of alcoholate reactants are sodium methylate, sodium ethylate, potassium methylate, potassium ethylate, lithium methylate, lithium ethylate, sodium propylate, potassium propylate, sodium isopropylate, potassium isopropylate, sodium butylate, sodium sec. butylate, potassium butylate, sodium amylate, potassium amylate, sodium 2-methylbutylate, sodium 3-methylbutylate, sodium methoxyethylate, potassium methoxyethylate, sodium octylate, sodium cyclohexylate, potassium cyclohexylate, sodium cyclopentylate, potassium cyclopentylate, sodium cyclooctylate, sodium benzylate, potassium benzylate.

An example of a silatrane which can be produced by the process of the invention is:

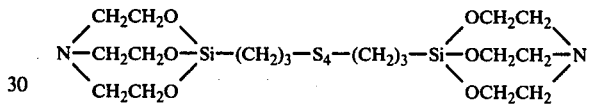

Bis-1,10(bicyclo[3,3,3]-1-aza-5-sila-4,6,11-trioxa-undecyl)-4,5,6,7-tetrathiadecane.

Silatrane group containing compounds of other structures which can be produced according to the process of the invention are described, for example, in the works of L. R. Garsen and L. K. Kerchner in "Journal of Pharmaceutical Sciences", Vol. 60 (1971), pages 1113 et seq., particularly page 1118 and of Voronkov et al. in Zh. Obshch. Khim., Vol. 45 (107) 1975, 7, 1649.

Unless otherwise indicated all parts and percentages are by weight.

The process of the invention can comprise, consist essentially of or consist of the steps set forth.

DESCRIPTION OF THE PREFERRED EMBODIMENTS

EXAMPLE 1

There were present in a two liter three-necked flask equipped with stirrer, internal thermometer, reflux condenser and solids supplying apparatus 500 ml of ethanol and 11.5 grams of sodium (0.5 mole) was dissolved therein with the development of hydrogen. After the end of the reaction at 45° C. there were then added 240.5 grams (1.0 mole) of 3-chloropropyltriethoxysilane. Then there were added 23.0 grams (0.5 mole) of NaSH and finally 48.0 grams (1.5 moles) of sulfur powder and subsequently the red colored reaction mixture was heated to 70° C. In the exothermic reaction the color changed gradually to yellow-gray. After heating to reflux temperature of about 80° C. for one and a half hours, it was cooled, the sodium chloride formed filtered off and the excess ethyl alcohol distilled off from the filtrate under reduced pressure.

There remained behind the light yellow bis-(3-triethoxysilylpropyl)-tetrasulfide in an amount of 255.0 grams which is 95.2% of theory. The named compound was identified by NMR and IR spectra and elemental analysis. The last named analysis gave the following values:

|  | C | H | Si | S |
|---|---|---|---|---|
| Calculated: | 40.11 | 7.84 | 10.42 | 23.79 |
| Found: | 38.20 | 7.43 | 9.82 | 23.46 |

The refractive index $n_D^{21}$ was 1.4937.

EXAMPLES 2 to 10

In the same way as in Example 1, additional organosilanes were produced employing the starting materials and with the analyses collected in Table I.

TABLE I

| | Starting Materials | | | | | Compound Produced | | | | |
|---|---|---|---|---|---|---|---|---|---|---|
| | | | | | | | Elemental Analysis in Weight % upper value : calculated lower values : found | | | |
| Example | Alcohol (ml) | Sodium (g) | Silane (g) | NaSH (g) | S (g) | Formula | C | H | Si | S |
| 2 | $C_2H_5OH$ 500 | 11.5 | $Cl(CH_2)_3Si(OC_2H_5)_3$ 240.8 | 23.0 | 32.0 | $[(C_2H_5O)_3Si(CH_2)_3]_2S_3$ | 42.65 40.94 | 8.35 8.04 | 11.08 10.64 | 18.98 18.22 |
| 3 | $C_2H_5OH$ 500 | 11.5 | $Cl(CH_2)_3Si(OC_2H_5)_3$ 240.8 | 23.0 | 16.0 | $[(C_2H_5O)_3Si(CH_2)_3]_2S_2$ | 45.53 44.17 | 8.92 8.64 | 11.83 11.48 | 13.51 13.10 |
| 4 | $CH_3OH$ 500 | 11.5 | $Cl(CH_2)_3Si(OCH_3)_3$ 198.8 | 23.0 | 48.0 | $[(CH_3O)_3Si(CH_2)_3]_2S_4$ | 31.69 30.42 | 6.65 6.38 | 12.35 11.88 | 28.20 27.51 |
| 5 | $CH_3OH$ 500 | 11.5 | $Cl(CH_2)_3Si(OCH_3)_3$ 198.8 | 23.0 | 32.0 | $[(CH_3O)_3Si(CH_2)_3]_2S_3$ | 34.09 33.07 | 7.15 6.93 | 13.29 12.89 | 22.75 22.09 |
| 6 | $CH_3OH$ 500 | 11.5 | $Cl(CH_2)_3Si(OCH_3)_3$ 198.8 | 23.0 | 16.0 | $[(CH_3O)_3Si(CH_2)_3]_2S_2$ | 36.89 35.42 | 7.74 7.43 | 14.38 13.85 | 16.42 15.78 |
| 7 | $C_2H_5OH$ 500 | 11.5 | $Cl(CH_2)_2Si(OC_2H_5)_3$ 226.8 | 23.0 | 48.0 | $[(C_2H_5O)_3Si(CH_2)_2]_2S_4$ | 37.62 36.49 | 7.50 7.28 | 11.00 10.63 | 25.10 24.39 |
| 8 | $C_2H_5OH$ 500 | 11.5 | $Cl(CH_2)_2Si(OC_2H_5)_3$ 226.8 | 23.0 | 32.0 | $[(C_2H_5O)_3Si(CH_2)_2]_2S_3$ | 40.13 39.33 | 8.00 7.82 | 11.73 11.50 | 20.09 19.66 |
| 9 | $CH_3OH$ 500 | 11.5 | $Cl(CH_2)_2Si(OCH_3)_3$ 184.7 | 23.0 | 48.0 | $[(CH_3O)_3Si(CH_2)_2]_2S_4$ | 28.15 27.03 | 6.14 5.91 | 13.16 12.64 | 30.05 29.15 |
| 10 | $CH_3OH$ 500 | 11.5 | $Cl(CH_2)_2Si(OCH_3)_3$ 184.7 | 23.0 | 32.0 | $[(CH_3O)_3Si(CH_2)_2]_2S_3$ | 30.43 29.27 | 6.64 6.37 | 14.23 13.68 | 24.37 23.40 |

What is claimed is:

1. A process for the production of sulfur containing organosilicon compounds of the formula (I) Z — Alk — $S_x$ — Alk — Z, where Z is the grouping:

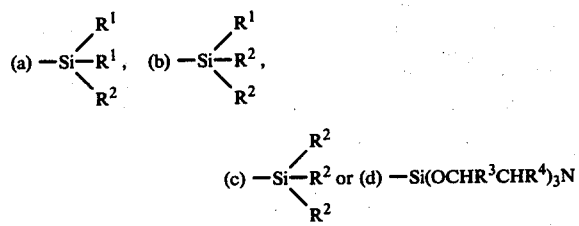

in which $R^1$ is an alkyl group having 1 to 5 carbon atoms, a cycloalkyl group with 5 to 8 carbon atoms, the benzyl group, phenyl or phenyl substituted with at least one methyl, ethyl or chloro group, $R^2$ is alkoxy of 1 to 4 carbon atoms, methoxyethoxy, cycloalkoxy with 5 to 8 carbon atoms, phenoxy or benzyloxy, $R^3$ and $R^4$ are alkyl of 1 to 3 carbon atoms or hydrogen, Alk is a divalent saturated hydrocarbon group having 1 to 5 carbon atoms or such a group interrupted by —O—, —S— or —NH— and x is a number from 2.0 to 6.0, said process comprising reacting an alkali metal alcoholate with a compound of the formula (II) Z — Alk — Hal, where Hal is chlorine, bromine or iodine with a hydrosulfide of the formula (III) MeSH, in which Me is ammonium, an alkali metal atom or an equivalent of an alkaline earth metal or zinc and with sulfur and removing the halide formed from the product.

2. The process of claim 1 wherein the reaction with the MeSH and sulfur is carried out in the presence of an organic solvent.

3. The process of claim 2 wherein the solvent comprises an alcohol.

4. The process of claim 2 where $R^2$ is alkoxy of 1 to 4 carbon atoms, methoxyethoxy, cycloalkoxy having 5 to 8 carbon atoms, phenoxy or benzyloxy and Z is (c).

5. The process of claim 4 wherein Alk is an alkylene group of 1 to 5 carbon atoms.

6. The process of claim 4 wherein Alk is an alkylene group of 2 to 5 carbon atoms.

7. The process of claim 5 wherein $R^2$ is alkoxy of 1 to 4 carbon atoms.

8. The process of claim 7 wherein $R^2$ is alkoxy of 1 to 2 carbon atoms and Alk is methylene, ethylene or trimethylene.

9. The process of claim 8 wherein the solvent is the alcohol corresponding to $R^2OH$.

10. The process of claim 1 wherein there is employed sodium, potassium, cesium or ammonium hydrosulfide in powder form and the sulfur is also employed in powder form.

11. The process of claim 10 wherein the reaction is carried out in solution in an alcohol at a temperature of 20° C. to the boiling point of the alcohol.

12. The process of claim 11 wherein the alcohol is an alkanol having 1 to 4 carbon atoms.

* * * * *